United States Patent [19]

Wilk

[11] Patent Number: 5,275,177
[45] Date of Patent: Jan. 4, 1994

[54] URINARY CATHETERIZATION DRAPE AND ASSOCIATED METHOD

[76] Inventor: Peter J. Wilk, 185 West End Ave., New York, N.Y. 10023

[21] Appl. No.: 906,935

[22] Filed: Jun. 30, 1992

[51] Int. Cl.$^5$ ............................................. A61D 19/00
[52] U.S. Cl. ..................................... 128/849; 128/854
[58] Field of Search .............. 604/327, 328, 329, 330, 604/331, 349, 351, 352; 128/849, 850, 853, 854, 761, 768

[56] References Cited

U.S. PATENT DOCUMENTS 3,762,399 10/1973 Riedell ................................. 604/408
3,799,161 3/1974 Collins ................................. 128/854
5,109,873 5/1992 Marshall .............................. 128/853

*Primary Examiner*—Randy C. Shay
*Attorney, Agent, or Firm*—R. Neil Sudol; Henry D. Coleman

[57] ABSTRACT

A urinary catheterization drape comprises a flexible sheet having an outer region and an inner region connected by a score line to enable a separation and removal of the inner region from the outer region. The inner region includes a substantially cylindrical projection which is closed at a free end. The cylindrical projection is provided at the free end with another score line extending perimetrically around the projection to enable a severance and removal of an end section of the projection.

6 Claims, 1 Drawing Sheet

5,275,177

URINARY CATHETERIZATION DRAPE AND ASSOCIATED METHOD

Background of the Invention

This invention relates to a urinary catheterization drape. This invention also relates to an associated method using the drape in performing a urinary catheterization.

A urinary catheter is inserted inwardly through a patient's urethra to the urinary bladder in order to implement an automatic drainage of urine from the bladder. Such a procedure is executed as a matter of course at the commencement of abdominal surgery to minimize the size of the bladder and thereby facilitate access to other organs in the abdomen.

In preparing the patient for receiving a urinary catheter, a drape sheet having a central opening is positioned over the patient's crotch. An antibacterial agent such as betadine is applied to the patient's skin in the area about the urethra and a catheter subsequently inserted. To insert a catheter into a male, the penis must be grasped with one hand and the catheter inserted with the other hand. This procedure complicates attempts to maintain sterility inasmuch as the hand touching the penis must be kept sterile prior to the procedure. This is difficult even if a new glove is put on the hand prior to catheterization.

OBJECTS OF THE INVENTION

An object of the present invention is to provide an improved catheterization procedure.

Another object of the present invention is to provide a catheterization drape for use in such a procedure.

Another, more particular, object of the present invention is to provide a catheterization drape which may be adapted for use on either a female or male patient.

A further particular object of the present invention is to provide a catheterization drape which enhances sterility of catheterization procedures, particularly in the case of a male patient.

Other objects of the present invention will be apparent from the detailed descriptions and drawings included herein.

SUMMARY OF THE INVENTION

A urinary catheterization drape comprises, in accordance with the present invention, a flexible sheet having an outer region and an inner region connected by a score line to enable a separation and removal of the inner region from the outer region. The inner region includes a substantially cylindrical projection which is closed at a free end. The cylindrical projection is provided at the free end with another score line extending perimetrically around the projection to enable a severance and removal of an end section of the projection.

In the event that the patient is a female, the inner region is removed from the outer region by tearing along the first score line. If the patient is a male, the first score line is left intact and the second score line is torn to enable a removal of the end section of the cylindrical projection.

Pursuant to another feature of the present invention, the sheet is rectangular and the first score line takes a rhombus shape.

A method for use in performing a urinary catheterization comprises, in accordance with the present invention, the steps of (a) providing a urinary catheterization drape, (b) severing a central portion of the drape from a peripheral portion of the drape by tearing along a score line defining a boundary between the central portion and the peripheral portion, (c) removing the central portion from the peripheral portion to form an aperture in the central portion, (d) positioning the peripheral portion over the patient so that the aperture is aligned with a urinary outlet port of the patient, and (e) inserting a urinary catheter into the patient's urethra through the aperture upon positioning of the peripheral portion of the drape over the patient.

Where the patient is a male, the peripheral portion includes a cylindrical projection having an open free end, while the central portion takes the form of a cup-shaped closure at the free end of the projection. The cup-shaped closure is removed in removal step (c). The penis of the patient is inserted into the cylindrical projection and is grasped through the material of the projection prior to catheter insertion.

Where the patient is a female, the central portion includes a cylindrical projection having a closed free end.

A catheterization procedure in accordance with the present invention uses a single drape which is readily adapted for use with either a female or a male patient. The catheterization drape enhances sterility of catheterization procedures, particularly in the case of a male patient.

DETAILED DESCRIPTION

Figure 1:
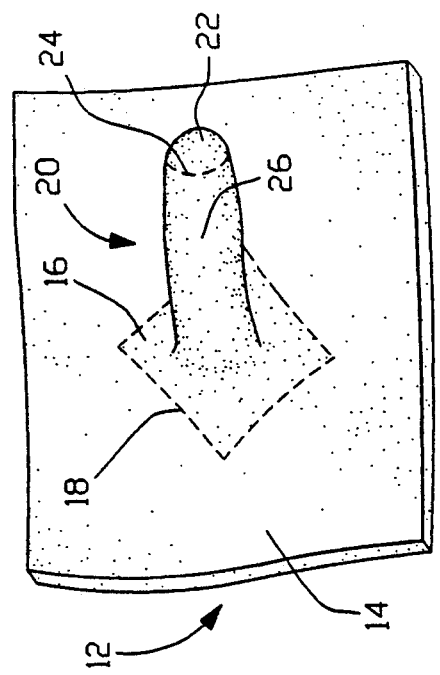
FIG. 1 is a schematic perspective view of a catheterization drape in accordance with the present invention, showing a central or inner region with a cylindrical, penis-receiving projection with a removed cup-shaped end section.

As illustrated in FIG. 1, a urinary catheterization drape comprises a flexible rectangular sheet 12 having an outer or peripheral region 14 and an inner or central region 16. Outer region 14 is connected to inner region 16 by a rhombus-shaped score line 18 which enables and facilitates a separation and removal of inner region 16 from outer region 14 prior to use of the drape during urinary catheterization of a female patient. Inner region 16 includes a substantially cylindrical projection 20 which is closed at a free end by a cup-shaped end section 22. Projection 20 is provided at the free end with a circular score line 24 which connects end section 22 to a body portion 26 of the cylindrical projection. Score line 24 extends perimetrically around projection 20 to enable a severance and removal of end section 22 prior to use of the drape during urinary catheterization of a male patient.

Figure 2:
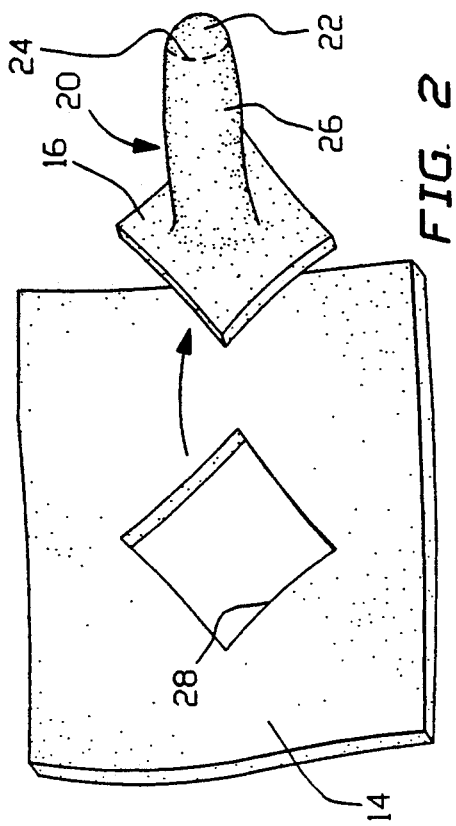
FIG. 2 is a schematic perspective view of a catheterization drape of FIG. 1, showing removal of the entire central or inner region in a procedure for using the drape on a female patient.

FIG. 2 shows the removal of inner region 16 from outer region 14. Score line 18 has been torn to separate inner region 16 from outer region 14. Upon the removal of inner region 16, outer region 14 is provided with a rhombus-shaped aperture 28. Inner region 16 is removed from outer region 14 prior to a positioning of the drape over the pelvis of a female patient. Alternatively, the drape may be positioned over the patient's pelvis prior to separation of inner region 16 from outer region 14. Upon the positioning of outer region 14 over a female patient's pelvis and an alignment of aperture 28 with the crotch area, a urinary catheter is inserted into the patient's urethra through aperture 28.

Figure 3:
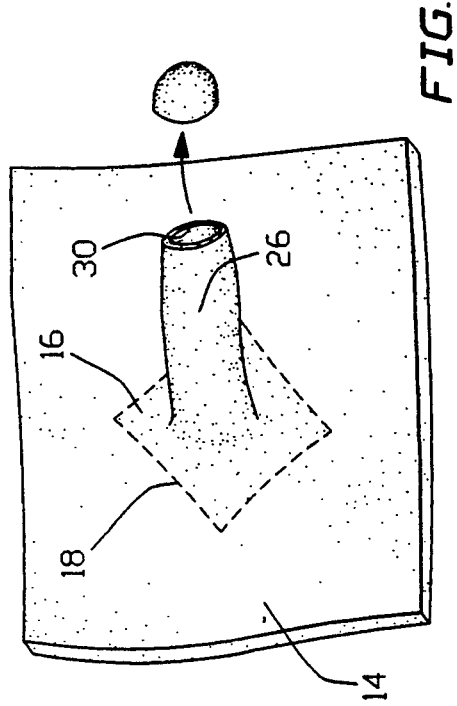
FIG. 3 is a schematic perspective view of a catheterization drape of FIG. 1, showing removal of the cup-shaped end section in a procedure for using the drape on a male patient.

FIG. 3 shows the removal of cup-shaped end section 22 from body portion 26 of cylindrical projection 20. Score line 24 has been torn to separate end section 22 from body portion 26. Upon the removal of end section 22, body portion 26 is provided with a circular aperture 30. End section 22 is removed from body portion 26 prior to a positioning of the drape over the pelvis of a male patient. Alternatively, the drape may be positioned over the patient's pelvis prior to separation of end section 22 from body portion 26. Upon the positioning of body portion 26 over a male patient's pelvis and an alignment of projection 20 with the crotch area, the patient's penis is manipulated through the medium of the drape and is inserted into body portion 26 of projection 20 so that the head of the penis is juxtaposed to aperture 30. Upon that juxtaposition, the penis is grasped through body portion 26 of projection 20 and a urinary catheter is inserted into the patient's urethra through aperture 30.

It is to be noted that in the case of a male patient, end section 22 may be understood as a central region of the drape while the remainder of the drape is a peripheral region. Accordingly, in either case, whether a female or male is being treated, a central section or region is removed from a peripheral region at the onset of a catheterization procedure.

Although the invention has been described in terms of particular embodiments and applications, one of ordinary skill in the art, in light of this teaching, can generate additional embodiments and modifications without departing from the spirit of or exceeding the scope of the claimed invention. For example, inner region 16 and concomitantly score line 18 may take any convenient form. In addition, outer region 14 of sheet 12 need not be flat but may have an inherent preformed shape conforming to a person's pelvis region. Accordingly, it is to be understood that the drawings and descriptions herein are profferred by way of example to facilitate comprehension of the invention and should not be construed to limit the scope thereof.

What is claimed is:

1. A method for use in performing a urinary catheterization of a male patient, comprising the steps of:
   providing a urinary catheterization drape having a substantially cylindrical projection with an aperture at a free end;
   inserting the penis of the patient into said projection so that said aperture is aligned with a urinary outlet port of the patient; and
   upon insertion of the penis of the patient into said projection and an alignment of said aperture with the urinary outlet port of the patient, inserting a urinary catheter into the patient's urethra through said aperture.

2. The method defined in claim 1, further comprising the steps of grasping the penis of the patient through said projection upon the insertion of the penis into said projection and maintaining a hold on the penis through said projection during the insertion of said urinary catheter into the patient's urethra.

3. A method for use in performing a urinary cauterization of a patient, comprising the steps of:
   providing a urinary catheterization drape having a peripheral portion and a central portion connected to one another along a first score line, said central portion including a substantially cylindrical projection having a free end, a cup-shaped closure portion being connected to said free end of said projection via a second score line;
   in the event that the patient is a female, severing said central portion of said drape from said peripheral portion of said drape by tearing along said first score line, and in the event that the patient is a male, severing said cup-shaped closure portion from said free end of said projection along said second score line;
   removing the severed portion of said drape from the remaining peripheral portion to form an aperture in said drape;
   positioning said peripheral portion over the patient so that said aperture is aligned with a urinary outlet port of the patient; and
   upon positioning of said peripheral portion over the patient, inserting a urinary catheter into the patient's urethra through said aperture.

4. The method defined in claim 3 wherein the patient is a male and said step of inserting includes the steps of inserting the penis of the patient into said projection, grasping the penis through said projection during the insertion of said urinary catheter into the patient's urethra.

5. A method for use in performing a urinary catheterization of a patient, comprising the steps of:
   providing a urinary catheterization drape having a peripheral portion and a central portion connected to one another along a score line, said central portion including a substantially cylindrical projection having a free end;
   in the event that the patient is a female, severing said central portion of said drape from said peripheral portion of said drape by tearing along said score line, removing the severed portion of said drape from the remaining peripheral portion to form an aperture in said drape, positioning said peripheral portion over the patient so that said aperture is aligned with a urinary outlet port of the patient, and, upon alignment of said aperture with the urinary outlet of the patient, inserting a urinary catheter into the patient's urethra through said aperture; and
   in the event that the patient is a male, inserting the penis of the patient into said projection so that an opening at said free end of said projection is aligned with a urinary outlet port of the patient, and, upon alignment of said opening with the urinary outlet of the patient, inserting a urinary catheter into the patient's urethra through said opening.

6. The method defined in claim 5 wherein the patient is a male, further comprising the steps of grasping the penis of the patient through said projection and maintaining a hold on the penis through said projection during he insertion of said urinary catheter into the patient's urethra.

* * * * *